(12) United States Patent
Conia et al.

(10) Patent No.: US 11,173,276 B2
(45) Date of Patent: Nov. 16, 2021

(54) CATHETER ASSEMBLY

(71) Applicant: W. L. Gore & Associates, Inc., Newark, DE (US)

(72) Inventors: Jerome S. Conia, Phoenix, AZ (US); Edward H. Cully, Flagstaff, AZ (US); Jeffrey B. Duncan, Flagstaff, AZ (US); James L. Goepfrich, Flagstaff, AZ (US); Woodrow W. Watson, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 103 days.

(21) Appl. No.: 15/578,613

(22) PCT Filed: Jun. 3, 2016

(86) PCT No.: PCT/US2016/035700
§ 371 (c)(1),
(2) Date: Nov. 30, 2017

(87) PCT Pub. No.: WO2016/196920
PCT Pub. Date: Dec. 8, 2016

(65) Prior Publication Data
US 2018/0154108 A1 Jun. 7, 2018

Related U.S. Application Data

(60) Provisional application No. 62/171,392, filed on Jun. 5, 2015.

(51) Int. Cl.
*A61M 25/00* (2006.01)
*A61M 31/00* (2006.01)
(Continued)

(52) U.S. Cl.
CPC .... *A61M 25/0026* (2013.01); *A61M 25/0023* (2013.01); *A61M 31/005* (2013.01);
(Continued)

(58) Field of Classification Search
CPC .......... A61M 25/0021; A61M 25/0023; A61M 25/0026; A61M 25/0097;
(Continued)

(56) References Cited

U.S. PATENT DOCUMENTS

| 3,981,299 | A |   | 9/1976 | Murray |
| 5,234,425 | A | * | 8/1993 | Fogarty ................ A61B 17/221 606/1 |

(Continued)

FOREIGN PATENT DOCUMENTS

| JP | 2018-516694 A | 6/2018 |
| JP | 2019-187759 A | 10/2019 |

(Continued)

OTHER PUBLICATIONS

International Search Report and Written Opinion from PCT/US2016/035700, dated Sep. 2, 2016, 15 pages.

*Primary Examiner* — Nathan R Price
*Assistant Examiner* — Dung T Ulsh

(57) ABSTRACT

A multi lumen catheter assembly. The assembly provides an expandable, low profile, fixed length sheath and catheter, with fixed infusion ports. The assembly has an expandable outer sheath that expands upon pressure activation with a fluid and the sheath allows the fluid to exit from at least one predetermined fixed location from a distal end of the catheter assembly. The catheter assembly can be used in various medical device procedures, such as a TIPS (Transjugular Intrahepatic Portosystemic Shunt) procedure, or anywhere a low profile, multi lumen, infusion catheter system is desired.

15 Claims, 15 Drawing Sheets

(51) Int. Cl.
*A61F 2/95* (2013.01)
*A61M 25/01* (2006.01)

(52) U.S. Cl.
CPC ............ *A61F 2/95* (2013.01); *A61M 25/0097* (2013.01); *A61M 2025/0024* (2013.01); *A61M 2025/0034* (2013.01); *A61M 2025/0035* (2013.01); *A61M 2025/0037* (2013.01); *A61M 2025/0039* (2013.01); *A61M 2025/018* (2013.01)

(58) Field of Classification Search
CPC .. A61M 2025/0024; A61M 2025/0025; A61M 2025/0034; A61M 2025/0035; A61M 2025/0037; A61M 2025/0039; A61M 2025/018
See application file for complete search history.

(56) References Cited

U.S. PATENT DOCUMENTS

| | | | |
|---|---|---|---|
| 6,179,827 B1 | 1/2001 | Davis et al. | |
| 8,852,112 B2 | 10/2014 | Bielewicz | |
| 2005/0085761 A1* | 4/2005 | Wang | A61M 1/3658 604/6.11 |
| 2006/0135981 A1* | 6/2006 | Lenker | A61M 25/0662 606/191 |
| 2007/0088323 A1* | 4/2007 | Campbell | A61M 25/10 604/523 |
| 2009/0209969 A1* | 8/2009 | Wolfe | A61B 1/00135 606/108 |
| 2009/0259089 A1 | 10/2009 | Gelbart et al. | |
| 2011/0152763 A1* | 6/2011 | Bishop | A61M 25/104 604/101.01 |
| 2011/0190683 A1* | 8/2011 | Gellman | A61M 25/0023 604/6.16 |
| 2011/0202067 A1* | 8/2011 | Falkner | A61B 17/3401 606/129 |
| 2011/0264133 A1* | 10/2011 | Hanlon | A61M 25/007 606/194 |
| 2012/0065579 A1 | 3/2012 | Cully | |
| 2014/0142427 A1 | 5/2014 | Petroff | |
| 2015/0306361 A1* | 10/2015 | Feig | A61M 25/1011 604/509 |
| 2016/0067444 A1* | 3/2016 | Allen | A61M 25/007 604/246 |

FOREIGN PATENT DOCUMENTS

| | | |
|---|---|---|
| JP | 2020-014893 A | 1/2020 |
| WO | 2005/023358 A1 | 3/2005 |
| WO | WO-2011097229 | 8/2011 |
| WO | WO-2014140093 | 9/2014 |

* cited by examiner

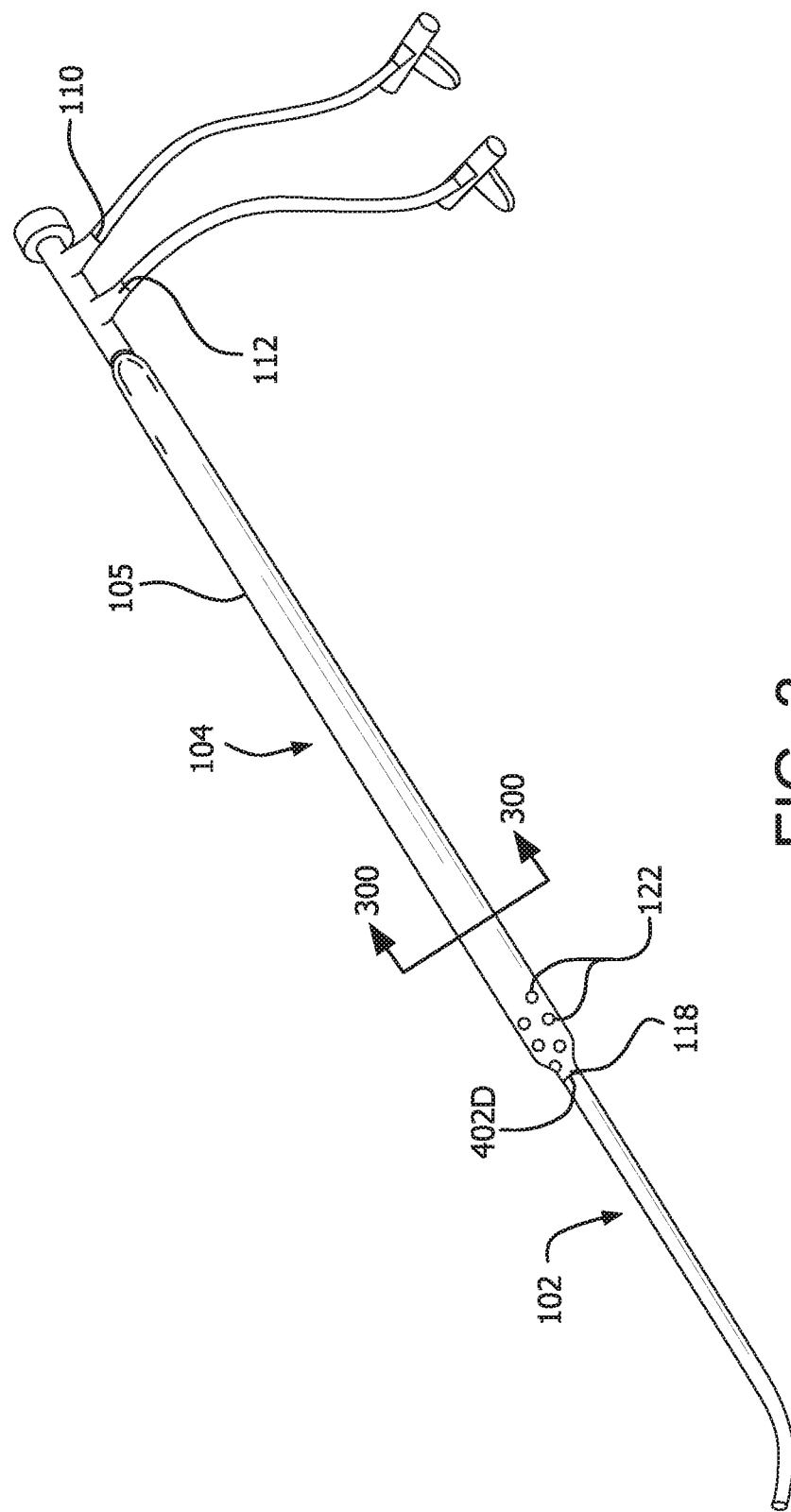

CATHETER ASSEMBLY

CROSS-REFERENCE TO RELATED APPLICATION

This application is a national phase application of PCT Application No. PCT/US2016/035700, filed Jun. 3, 2016, which claims priority to U.S. Provisional Application No. 62/171,392, filed Jun. 5, 2015, both of which are herein incorporated by reference for all purposes.

FIELD

The present disclosure relates to catheters associated with implantable medical devices and, more particularly, relates to low profile catheter assemblies with multiple channels capable of delivering fluids to multiple locations.

BACKGROUND

The use of implantable medical devices in the treatment of diseased vasculature and other body conduits has become commonplace in the medical field. Such devices can be surgically implanted in or delivered endoluminally to the treatment site. In the latter case, visualization of the vasculature and the device can be challenging. Typically, caregivers and/or operators use a catheter for injection contrast to aid in visualization during the treatment. Moreover, vessel hydration or delivery of medicaments to the anatomy in association with delivery of such devices may be desirable. A catheter has a profile that indicates what size introducer the catheter can be inserted through. Adding multi lumen capabilities to a catheter tends to increase the overall catheter profile. In some previously known catheters, an additional lumen means having multiple fixed lumen diameters (i.e., the lumen diameters do not change significantly under normal operating procedures) and thereby having an increased profile compared to a single lumen catheter. In some other previously known catheters, an expandable sheath is used as a secondary lumen and at least partially addresses the increased profile by allowing the expandable sheath to expand and contract.

These previously known catheters still have limitations and leave room for improvements, especially in difficult procedures. Therefore, it remains desirable to provide a multi-channel catheter that facilitates accurate and efficient endoluminal deployment of implantable devices and endovascular tools.

SUMMARY

Various examples of catheter assemblies and associated systems and methods in accordance with the present disclosure relate to medical devices with multiple lumens usable for delivery of fluid(s) to one or more desired locations in the anatomy. In some examples, a catheter assembly in accordance with the present disclosure is usable to deliver fluids (e.g., contrast solution or fluid) to desired location(s) in body lumens, such as the vasculature of a patient (e.g., in the region of a portosystemic shunt, the aorta, or other vasculature either venous or arterial).

In some examples, a catheter assembly in accordance with the present disclosure includes a sheath attached to an elongated member of a medical device (e.g., a shaft and/or hub of a catheter assembly) at one or more attachment location(s) to form one or more lumens for fluid delivery. Some examples relate to a catheter assembly having an elongated tubular element (e.g., a catheter shaft, a balloon catheter, etc.) with an outer surface, a first end and a second end, a length extending between the first end and the second end, and a lumen extending along the elongated element. A sheath surrounds at least a portion of the length of the elongated element, wherein the sheath comprises a wall thickness, an outer surface area, a first relaxed configuration and a second pressurized configuration. In some examples, the sheath is attached to the elongated element at opposing circumferential ends of the sheath and cooperates with the elongated element to form one or more channels along at least a portion of the length of the elongated element when the sheath is in the second pressurized configuration. In some examples, the sheath comprises at least one macroscopic aperture through the wall thickness. In some examples, the at least one macroscopic aperture(s) have a macroscopic aperture area, wherein the macroscopic aperture area of the macroscopic aperture(s) occupies 20% or less of the surface area of the sheath.

BRIEF DESCRIPTION OF THE DRAWINGS

The accompanying drawings are included to provide a further understanding of the present disclosure and are incorporated in and constitute a part of this specification, illustrate embodiments of the present disclosure, and together with the description serve to explain the principles of the present disclosure.

FIG. 3 shows an isometric view of a catheter with an expanded outer sheath in accordance with the present disclosure.

DETAILED DESCRIPTION

In some examples, catheter assemblies according to the present disclosure are usable to deliver fluids to vasculature or other locations in a body. For example, a catheter assembly may transport contrast fluid within the body, or any of a variety of fluids including saline, medicaments (pharmaceutical or other therapeutic agents), blood, serum, or other fluids as desired.

Figure 1:
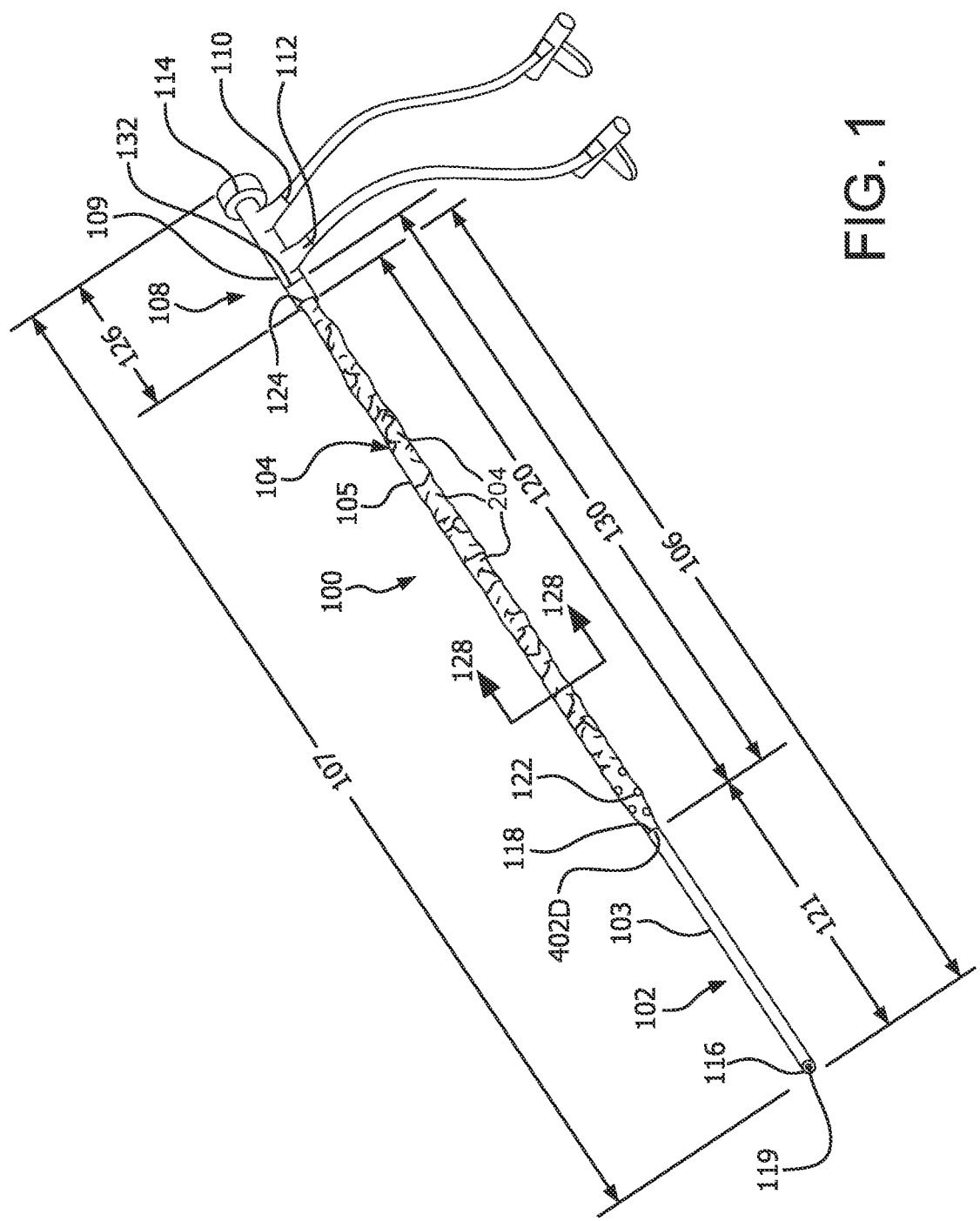
FIG. 1 shows an isometric view of a catheter with a relaxed outer sheath in accordance with the present disclosure.

In various examples, catheter assemblies described herein have an additional component or layer added along the catheter to aid in delivering fluids within the body. This additional layer may be surrounding at least a portion of an outer surface of the catheter. For example, as shown in FIG. 1, a catheter assembly 100 has an elongate member 102 (e.g., a catheter, guidewire, tube, etc.), a hub 108 with a hub proximal side delivery port 110, a hub distal side delivery port 112, a hub proximal end fluid delivery port 114, and a hub distal end 124 with a port, and an additional layer (e.g., a sheath 104) along the catheter outer surface 103. A catheter typically has an outside diameter and an inside diameter, thereby having a lumen at least partially along the catheter.

As shown in FIG. 1, the catheter assembly 100 defines a catheter assembly length 107. As also shown, the sheath 104 defines a first sheath length 130 (e.g., corresponding to a total length of the sheath 104 between proximal and distal ends) and a second sheath length 120 (e.g., corresponding to a length of the sheath 104 from a distal end of the hub to the distal end of the sheath 104). As shown, the catheter assembly length 107 extends between hub proximal end port 114 and catheter assembly distal end 116 and measures between hub proximal end port 114 and catheter assembly distal end 116 longitudinally along elongated element 102 (a catheter as shown, although other elongated elements are contemplated as previously described). As also shown, the first sheath length 130 extends between sheath proximal end 132 and sheath distal end 118 longitudinally along catheter 102. The proximal end 132 of sheath 104 may extend to any location along hub length 126 as desired. As shown, the second sheath length 120 is defined between hub distal end 124 and sheath distal end 118. Sheath 104 may extend along a length portion of catheter 102 as desired (e.g., along catheter outer surface 103) and along at least a portion of hub 108 as desired (e.g., along hub outer surface 109).

The desired attachment location(s) between the elongate member 102 and the sheath 104, the catheter assembly length 107, the catheter effective length 106, the first sheath length 130 and the second sheath length 120 may vary per application and therefore may vary sheath offset length 121. For example, the catheter assembly length 107 may be 40 cm (in other cases the catheter assembly length may be 50 cm, 60 cm, or 70 cm or more). For example, the sheath offset length 121 may be 10 cm. In other cases, the sheath offset length 121 may be 8 cm, 6 cm, 4 cm or less. In a TIPS (Transjugular Intrahepatic Portosystemic Shunt) application, a sheath offset length 121 of 10 cm may be useful for a typical anatomy. Hub length 126 extends between hub proximal end port 114 and hub distal end 124.

The sheath 104 and the sheath apertures 122 have associated surface areas. The sheath apertures 122 can encompass varying amounts of area and therefore varying ratios of the sheath 104 total surface area. For example, the sheath apertures 122 surface area may account for approximately 20% of the total surface area of the sheath 104. In other cases, the sheath apertures may account for 18%, 16%, 14%, 12%, 10%, 5%, 1%, or even less than 1%. The area calculations are taken when the catheter assembly is in a non-pressurized state as shown in FIG. 1. The sheath aperture areas and sheath areas can be measured using standard known area calculating techniques. A sheath aperture is considered macroscopic if fluid can be passed through the aperture by a syringe under normal clinical operating pressures.

In some examples (e.g., as shown in FIGS. 1, 3, 5A, 5B and 5C) the sheath 104 is attached circumferentially to the catheter 102, at a location distal to at least one of the macroscopic sheath apertures 122. As shown, the sheath 104 is also attached circumferentially to another portion of the catheter assembly 100 at an opposing end of the sheath 104 (e.g., at an intermediate location on catheter 102, at a distal end of catheter 102, or at another location along catheter 102 as desired).

Figure 2A:
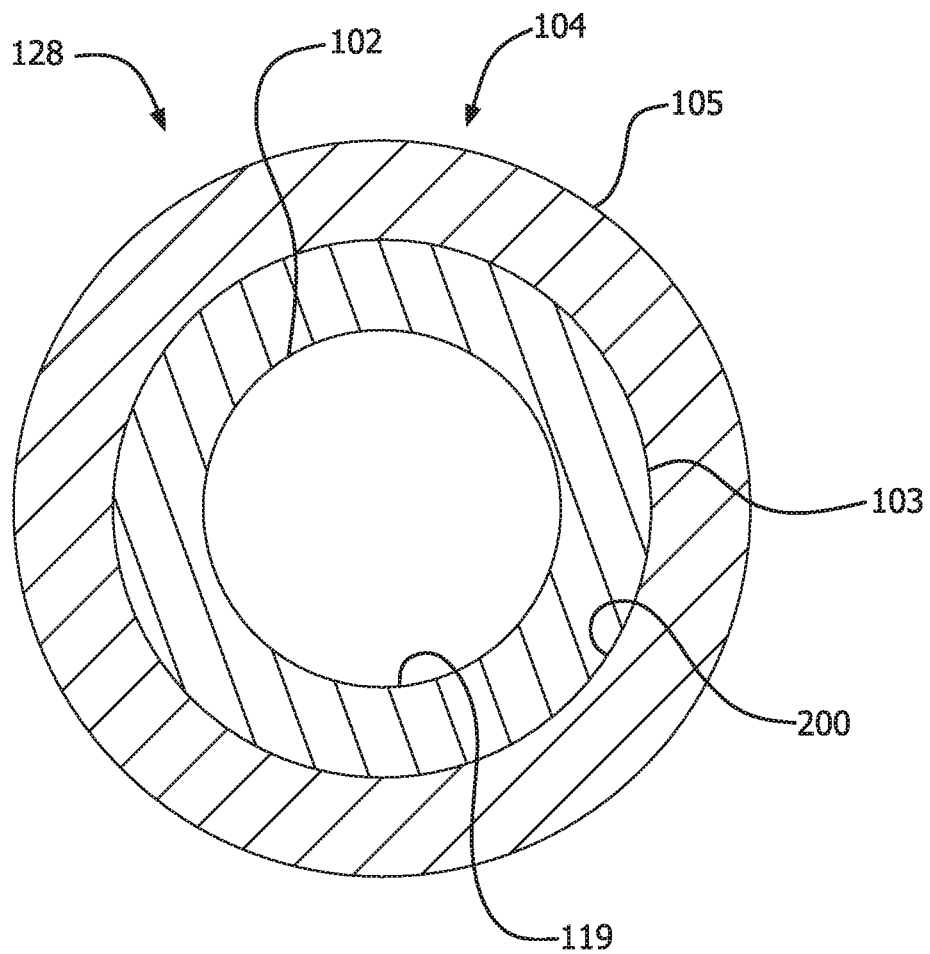
FIGS. 2A-2D show transverse cross sections taken at a location along a length of several embodiments of a catheter assembly in accordance with the present disclosure.
Figure 2B:
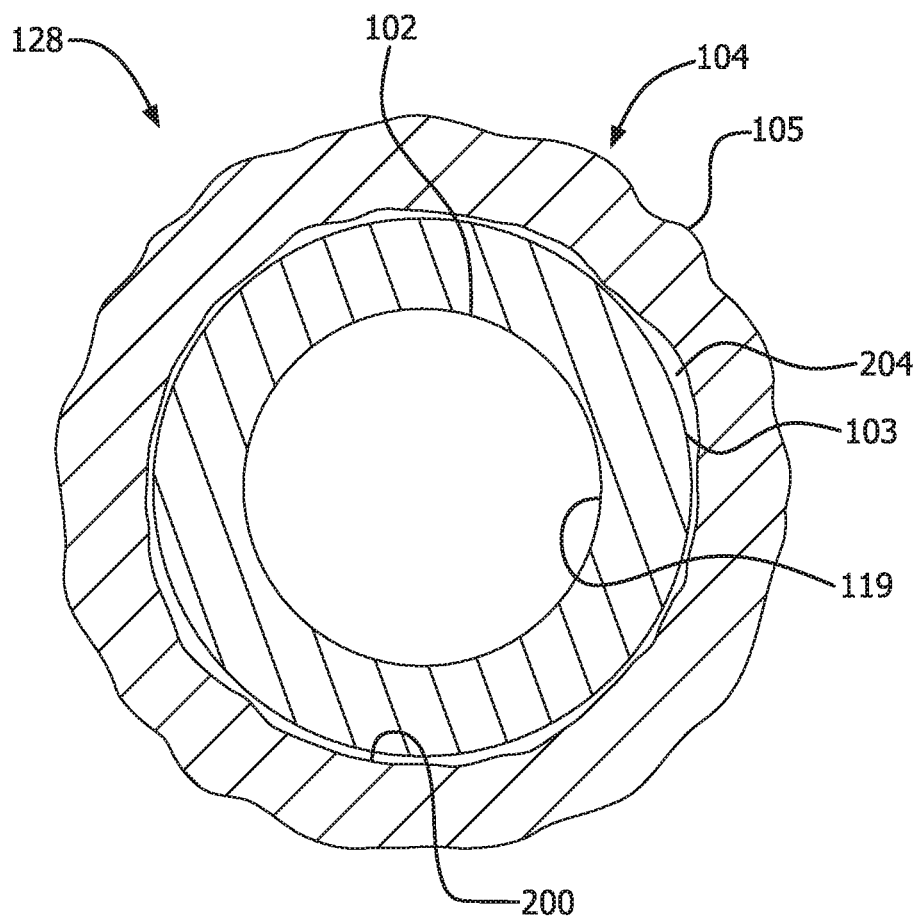

In various ways, a sheath can surround a catheter. For example, as shown in transverse cross section 128 of catheter assembly 100 in FIG. 2A, the sheath 104 may more tightly surround catheter 102. Sheath inner surface 200 may be in contact entirely with catheter outer surface 103, thereby having no significant voids or sheath pockets 204 (e.g., transverse cross section 128 of catheter assembly 100 in FIG. 2B). Alternatively, as shown in FIG. 2B, the sheath 104 may be more loosely fitted along the catheter 102. Sheath inner surface 200 may partially contact catheter outer surface 103, thereby creating sheath pockets 204 along the catheter outer surface 103. The sheath pockets 204 tend to be more localized and not run a continuous channel between sheath apertures 122 and hub distal fluid delivery port 112. In each of these examples, the sheath 104 is in a relaxed configuration (i.e., not pressurized by an externally supplied force, e.g., a syringe). Sheath 104 may subsequently be expanded by an externally supplied force (e.g., to produce an internal fluid pressure in the channel) supplied by an external pressure device (e.g., a syringe) to create a fluid channel(s) 400, 401 as shown in transverse cross sections 300 of catheter assembly 100 in FIGS. 2C and 2D (see also FIG. 4C).

In some examples, the sheath 104 is configured to be distended by an internal pressure and to elastically recover upon removal of the internal pressure. Additionally or alternatively, the sheath 104 can be loosely fitted around the catheter 102 such that upon internal pressurization the loose portions of the sheath 104 are expandable to a pressurized configuration and upon removal of the internal pressurization the loose portions of the sheath 104 return to the relaxed configuration. The sheath 104 is optionally formed of fluoropolymer materials, such as expanded PTFE ("ePTFE"), or other materials such as silicone, polyurethane, polyethylene terephthalate or others. In some examples, the sheath 104 includes one or more elastic layer(s) or component(s), such as a separate elastomeric layer (e.g., a silicone or polyurethane layer) or an elastomer component within a layer (e.g., silicone coated onto or imbibed within an ePTFE layer).

Figure 2C:
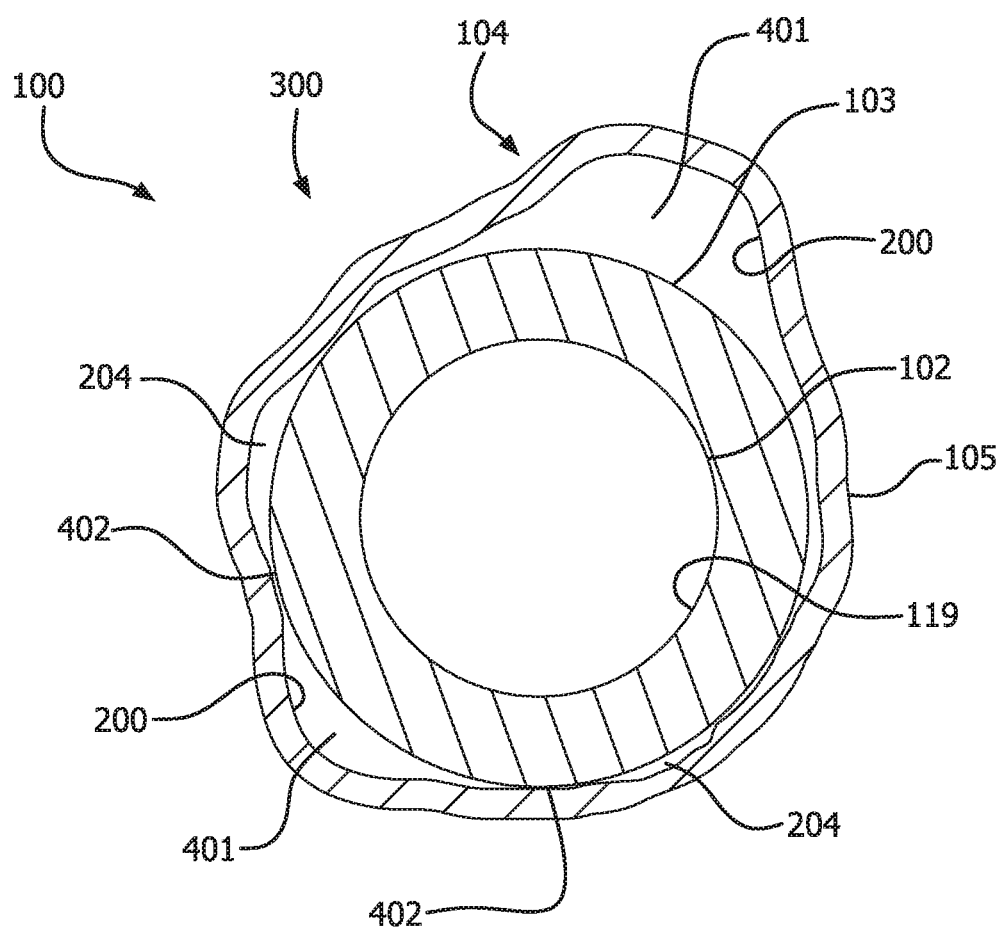
Figure 2D:
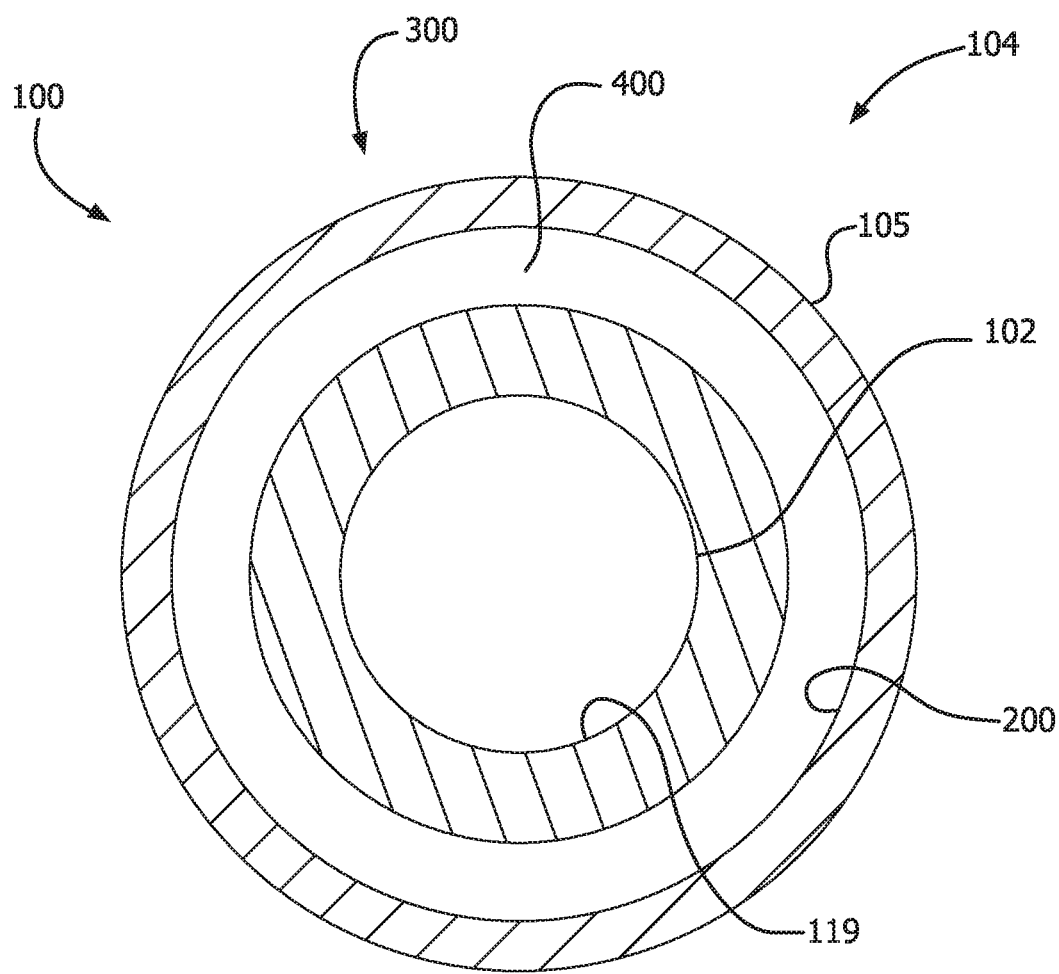

In some examples, the catheter assembly 100, and in particular the sheath 104, has a first relaxed configuration circumference and a second pressurized configuration circumference that is greater than the first relaxed configuration circumference. For example, as shown in FIG. 2C, FIG. 2D, and FIG. 4C, a length (e.g., a circumference) along sheath outer surface 105 in a pressurized configuration is greater than a length (e.g., a circumference) along sheath outer surface 105 in a non-pressurized configuration. In some examples, the sheath 104 transitions to the pressurized configuration upon application of an internal fluid pressure. After pressure (e.g., internal fluid pressure) has been released, the sheath returns towards its original non-pressurized configuration. As previously referenced, any of a variety of fluids may be used for pressurization, including contrast solution, saline, medicaments, blood, serum, or other fluids.

In various embodiments, a sheath may transition from a resting configuration towards a pressurized configuration upon pressurizing the sheath (e.g., with an internal fluid pressure). Transverse cross sections 128 of catheter assembly 100 (as shown in FIGS. 2A, 2B, and FIGS. 4A, 4B) show a sheath 104 in a relaxed, resting state against the catheter 102. When the sheath is pressurized through at least one of two side hub ports (e.g., 112 as shown in FIG. 5A), the sheath 104 moves away from the catheter 102 towards a more pressurized, non-relaxed configuration, as shown in various pressurization stages as shown by FIGS. 2C, 2D, and FIG. 3. For example, a partial fluid channel(s) 401 may form, urging the sheath 104 away from the catheter 102, as shown in transverse cross section 300 of catheter assembly 100 in FIG. 2C, when a continuous space forms from a hub port (e.g., hub distal fluid delivery port 112) to sheath apertures 122. The partial fluid channel(s) 401 may transition into a sheath full fluid channel 400, as shown in transverse cross section 300 of catheter assembly 100 in FIG. 2D when the catheter assembly is in a pressurized configuration. The sheath full fluid channel 400 forms when a fluid urges the entire sheath inner surface 200 away from a contacting surface (e.g., a catheter outer surface 103 or hub outer surface 109) entirely and forms a continuous space from a hub port (e.g., hub distal fluid delivery port 112) and sheath apertures 122. Alternatively, the partial fluid channel(s) 401 may form (FIG. 2C) and not transition into a sheath full fluid channel 400 (as shown in FIG. 2D). For example, by selectively keeping portions of the sheath 104 against catheter outer surface 103 (e.g., by tacking down or adhering portions of the sheath 104 to catheter 102 at desired attachment location(s) 402 as shown in FIG. 2C). The attachment location(s) 402 attach, press, or keep portions of the sheath 104 (or in some other fashion) against catheter outer surface 103.

A catheter assembly may have multiple fluid channels. As shown by example in FIG. 2D, a catheter assembly 100 may have a first fluid channel (e.g., a catheter lumen 119) associated with a fluid delivery port 110 (as shown in FIG. 1) and a second fluid channel (e.g., 400,401) that is associated with a fluid delivery port 112 (as shown in FIG. 1). One or both of the fluid channels are configured to receive and convey pressurized fluids, for example.

In various ways, a sheath may be attached to a catheter. For example, the sheath 104 may be attached at one or more attachment location(s) 402. In some examples, the sheath 104 is attached at sheath distal end 118 as shown in FIG. 1 and FIG. 3 at attachment location 402D, although intermediate or proximal locations are additionally or alternatively contemplated. The attachment location(s) 402 may be entirely around a catheter 102 circumference at a location along catheter effective length 106 as shown in FIG. 1 and FIG. 3. Alternatively, the attachment location(s) 402 may not be sealed totally against the catheter 102 (e.g., not sealed against the catheter 102 at the sheath distal end 118). In some examples where the attachment location 402D is not sealed totally against the catheter, the sheath 104 allows some fluid to travel along the sheath 104 and to exit past the sheath distal end 118 and in some cases exit through sheath apertures 122 and past sheath distal end 118. The attachment location(s) 402 may help build pressure within the sheath 104 allowing the sheath to expand when fluid is injected. The attachment location(s) 402 also may help keep the sheath 104 at a fixed location along the catheter 102.

Figure 4A:
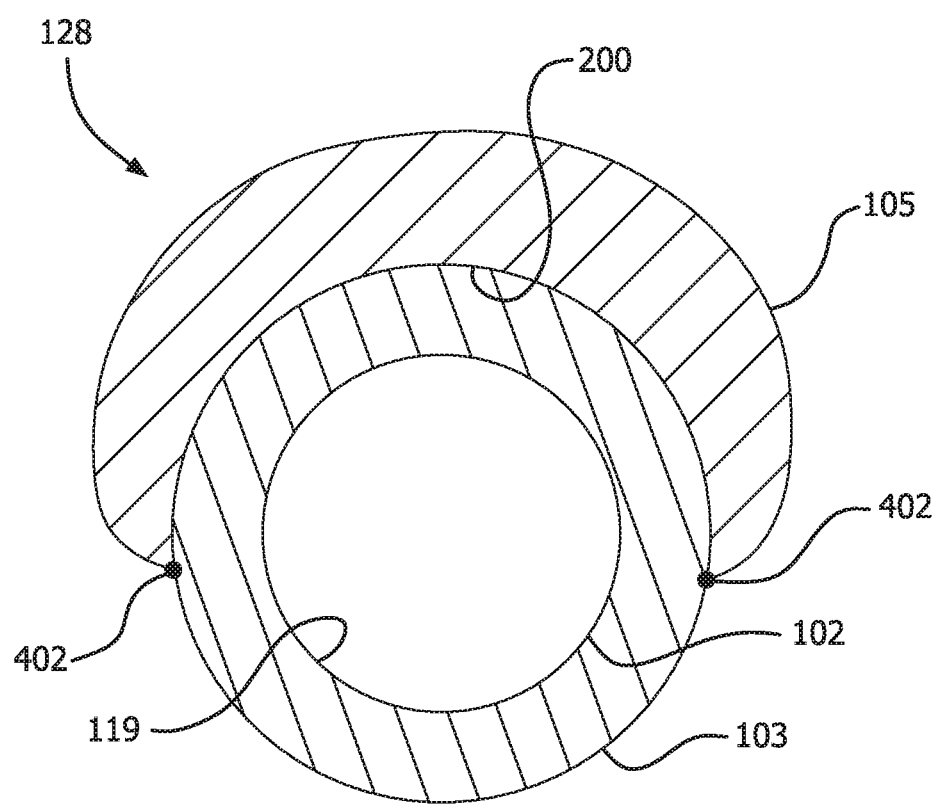
FIGS. 4A-4C show transverse cross sections taken at a location along a length of several embodiments of a catheter assembly in accordance with the present disclosure.
Figure 4B:
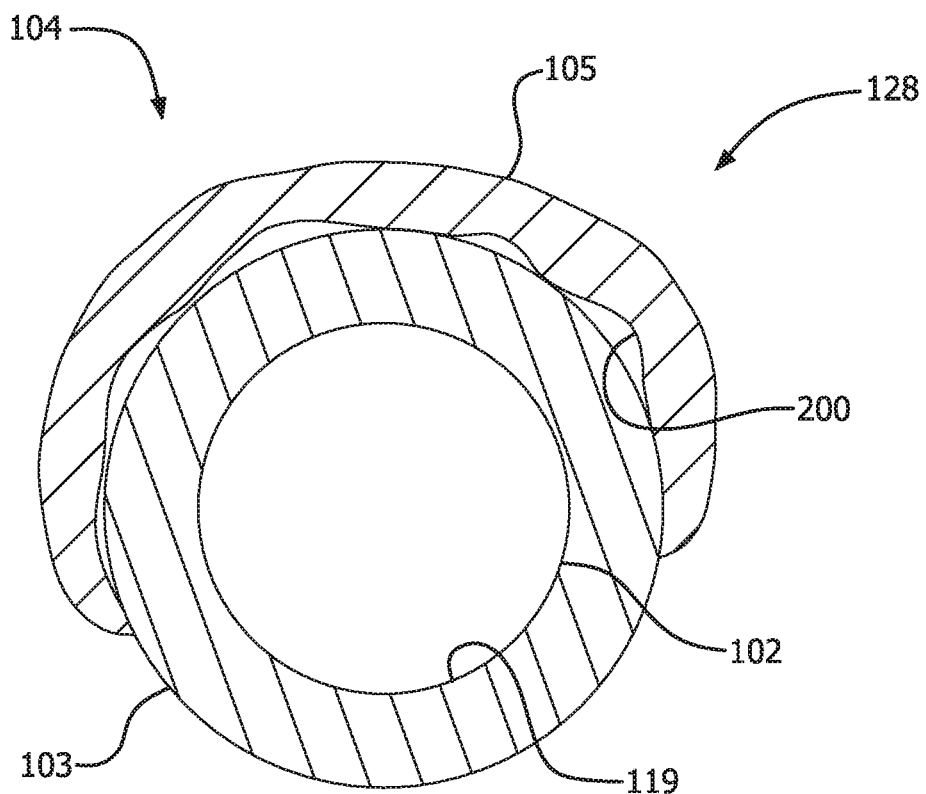
Figure 4C:
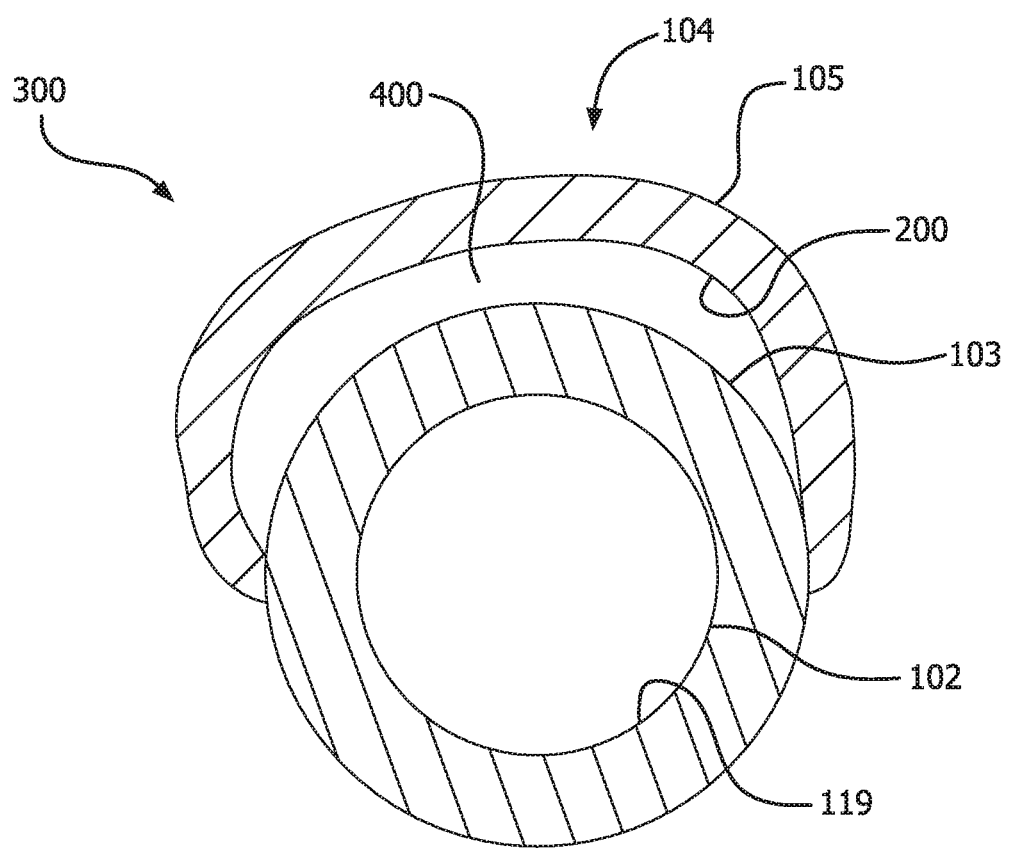
Figure 5A:
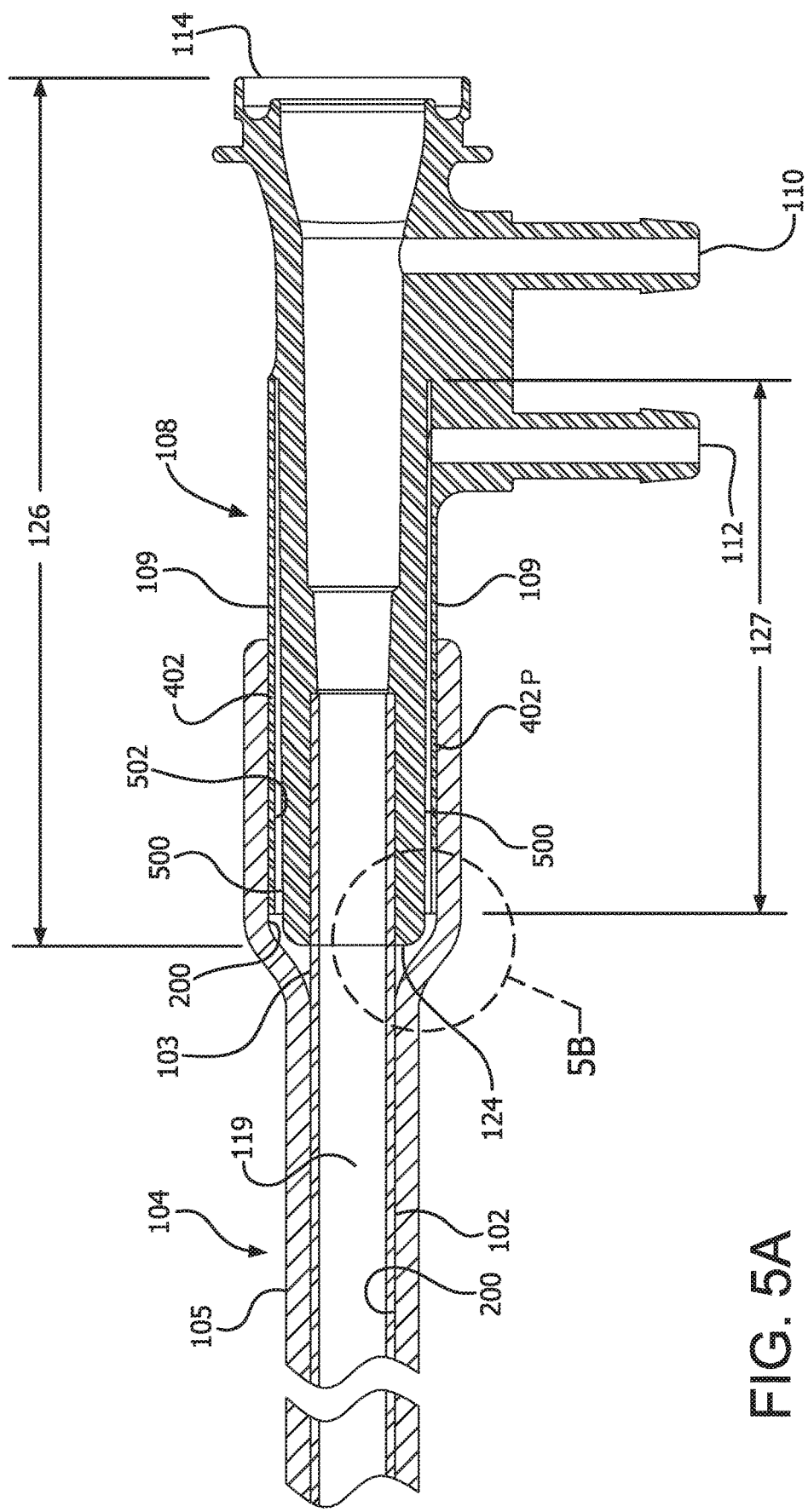
FIGS. 5A-5D show longitudinal cross sections of a catheter, hub, and sheath in accordance with the present disclosure.

The sheath 104 may also bound (surround) the catheter 102 but only partially around the catheter outer surface 103 for a given transverse cross section 128 as shown in FIG. 4A and FIG. 4B. This may help keep a lower profile than a sheath that entirely surrounds catheter 102, while still allowing a fluid channel to form along the catheter 102 and sheath 104 and exit sheath apertures 122 at a fixed location along the catheter 102. FIG. 4C shows a sheath 104 partially surrounding a catheter 102 with a sheath full fluid channel 400 (e.g., after being pressurized by an external pressure source).

Figure 5B:
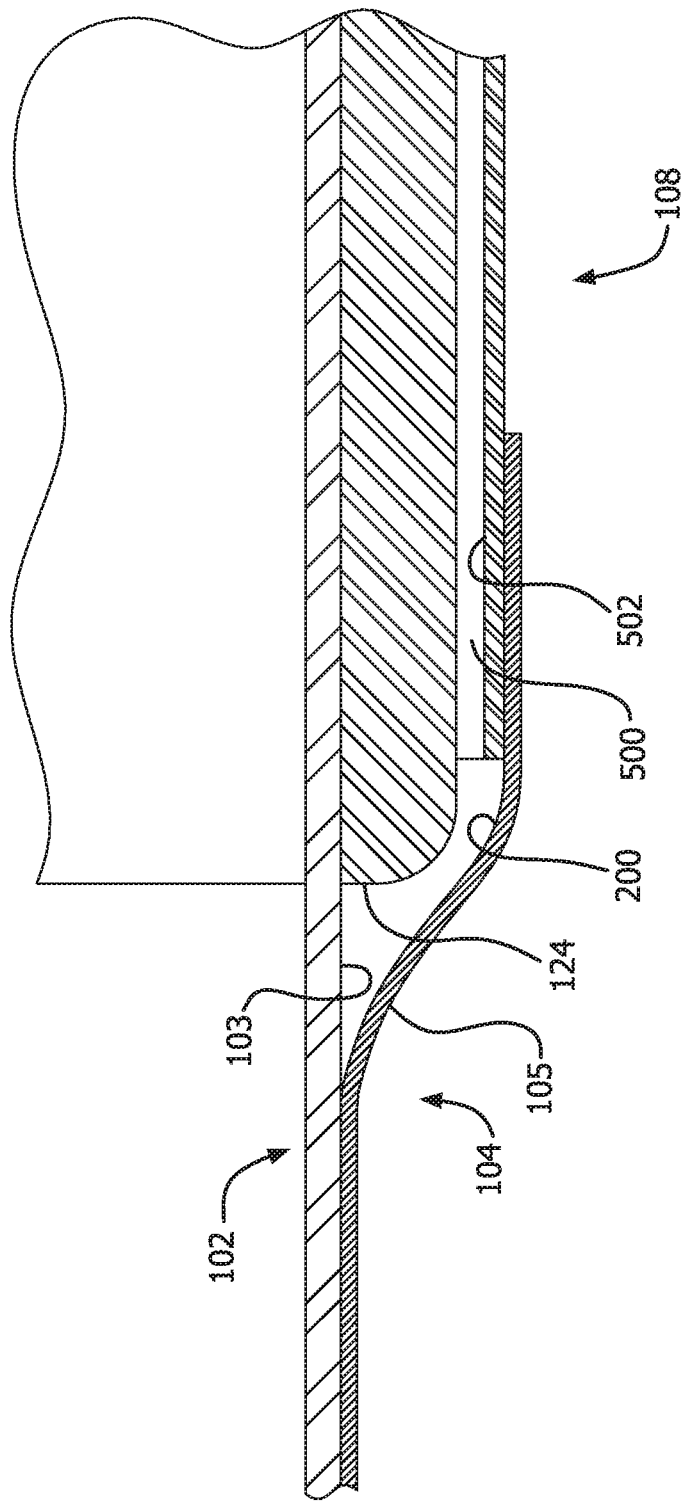

FIGS. 5A and 5B show a magnified longitudinal cross section view of hub 108, catheter 102, and sheath 104 in accordance with this disclosure (with FIG. 5B describing an enlarged portion of FIG. 5A). The hub 108 has a plurality of fluid delivery ports (first and second side ports as shown in FIGS. 1, 5A and 5B), including a hub distal delivery port 112 and a hub proximal delivery port 110, each of which can be used to deliver a fluid to one or more locations (e.g., contrast solution or another fluid at two separate, first and second locations along the length of the catheter 102). A fluid may be injected through the hub distal fluid delivery port 112 into a hub fluid space 500. In one example, the hub fluid space 500 is a toroidal shape (e.g., in a transverse cross section taken transversely to hub fluid space length 127), as shown in FIG. 5A and FIG. 5B. The hub fluid space 500 may vary along hub fluid space length 127 as shown in FIG. 5A (or alternatively may have constant dimensions along the hub fluid space length 127). The toroidal shape may allow a fluid to more easily expand the sheath 104 in an annular fashion by allowing fluid to more easily fill sheath inner surface 200. The fluid space 500 may have other features such as protrusions that may rifle or spin the fluid along the hub fluid space length 127 and along the sheath 104 and catheter 102. In other examples, the hub fluid space 500 may be a channel or lumen that is not annular.

In various ways, sheath 104 may attach to hub 108. In one example, as shown in FIG. 5A, the sheath 104 surrounds hub outside surface 109. The sheath 104 is attached along hub outside surface 109 and sheath inner surface 200 at one or more attachment location(s) 402, such as a proximal attachment location 402P, so fluid will not leak between the sheath 104 and the hub outside surface 109.

Figure 5C:
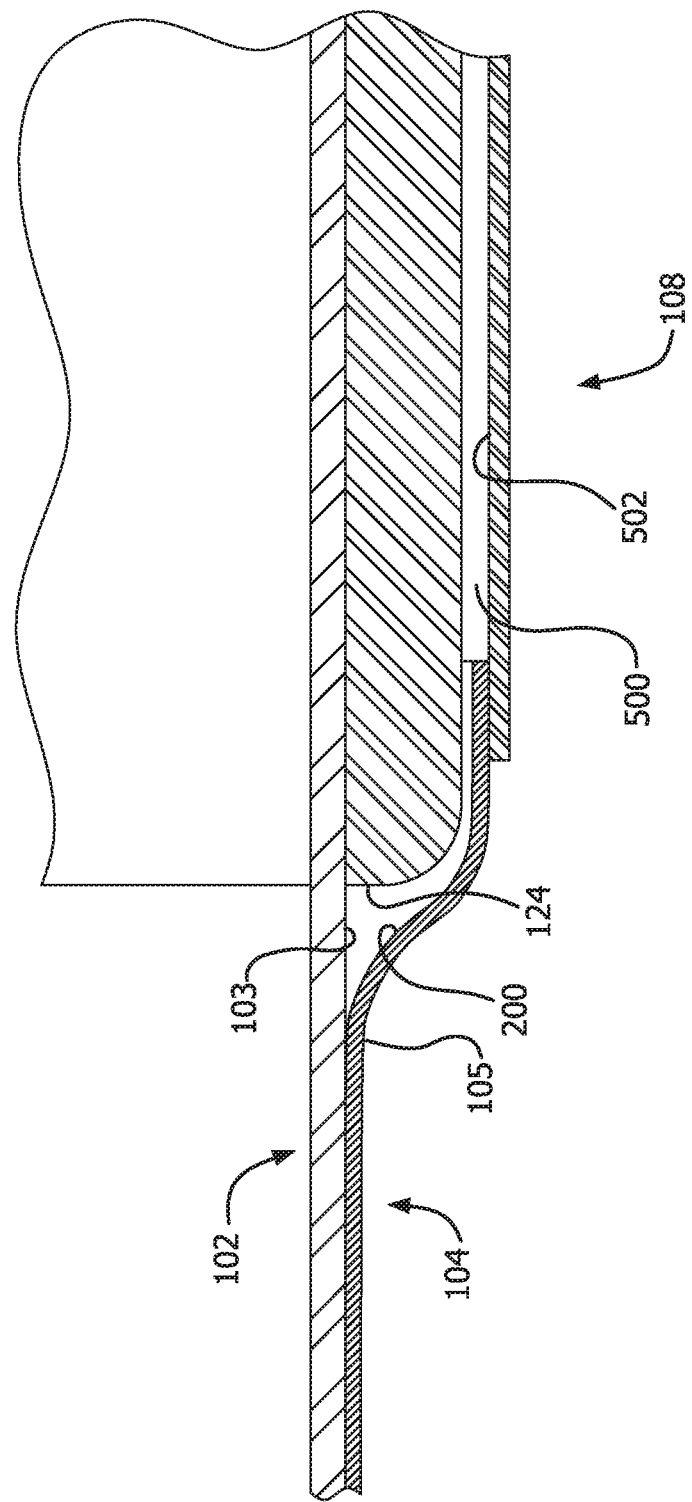

In another example, the sheath 104 is sealed along hub fluid space 500. Sheath outer surface 105 is sealed along hub fluid space inner surface 502, as shown in FIG. 5C.

Figure 5D:
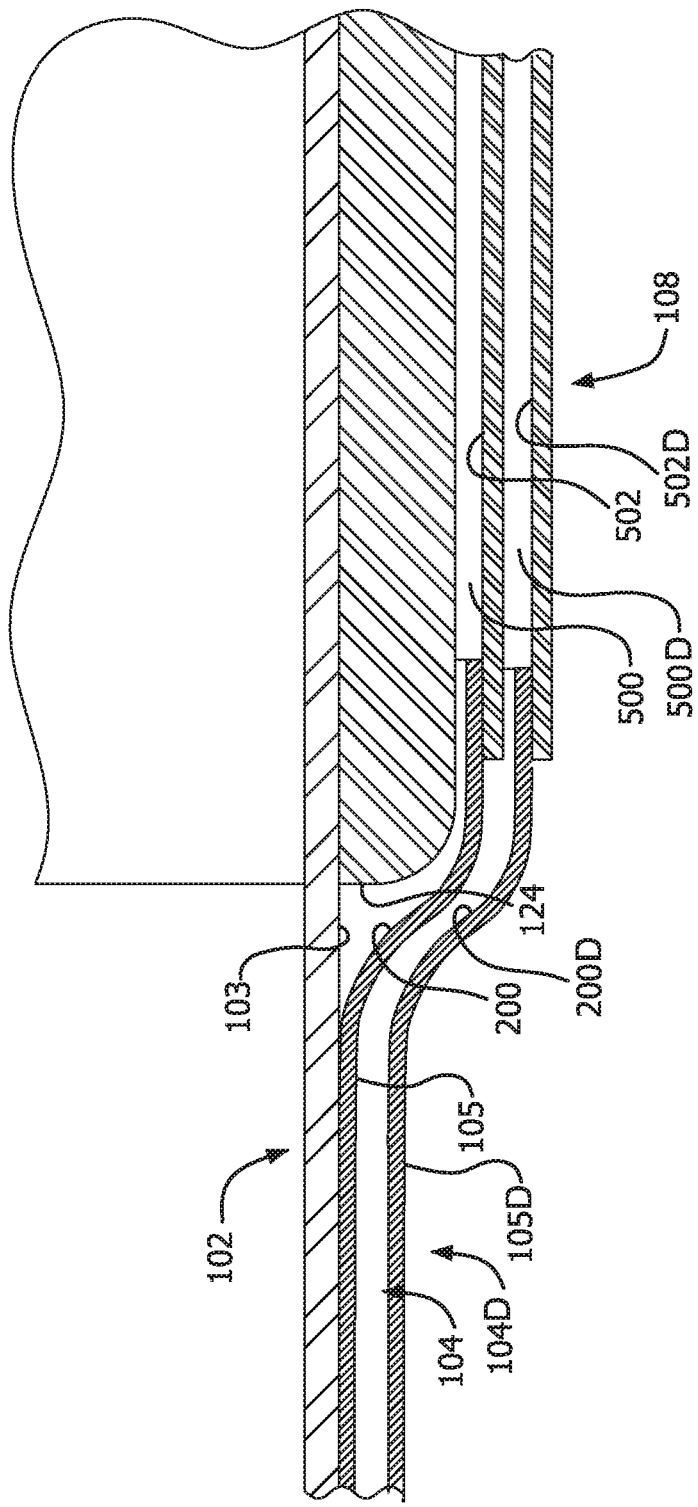

In still other examples, multiple sheaths (e.g., multiple, concentric sheaths) are attached to the hub 108 to form multiple fluid spaces. For example, FIG. 5D shows sheath 104 surrounding catheter 102 and sheath 104D concentrically surrounding sheath 104 and catheter 102 to form multiple sheath fluid channels. Hub 108 defines more than one fluid space, such as fluid space 500 and fluid space 500D. Each of the fluid spaces 500, 500D is in communication with a fluid port (not shown) of the hub 108. As shown, sheath outer surface 105 is sealed along hub fluid space inner surface 502 and sheath outer surface 105D is sealed along hub fluid space inner surface 502D. In various examples, the sheaths 104, 104D are configured to deliver a fluid through the fluid channels defined between sheath inner surface 200 and the catheter outer surface 103 and between the sheath inner surface 200D and sheath outer surface 105. The sheaths 104, 104D may be different lengths and have different distal openings and/or macroscopic apertures as desired. Additionally, the sheath 104D is optionally secured to the sheath 104 at one or more desired attachment location(s).

Figure 6:
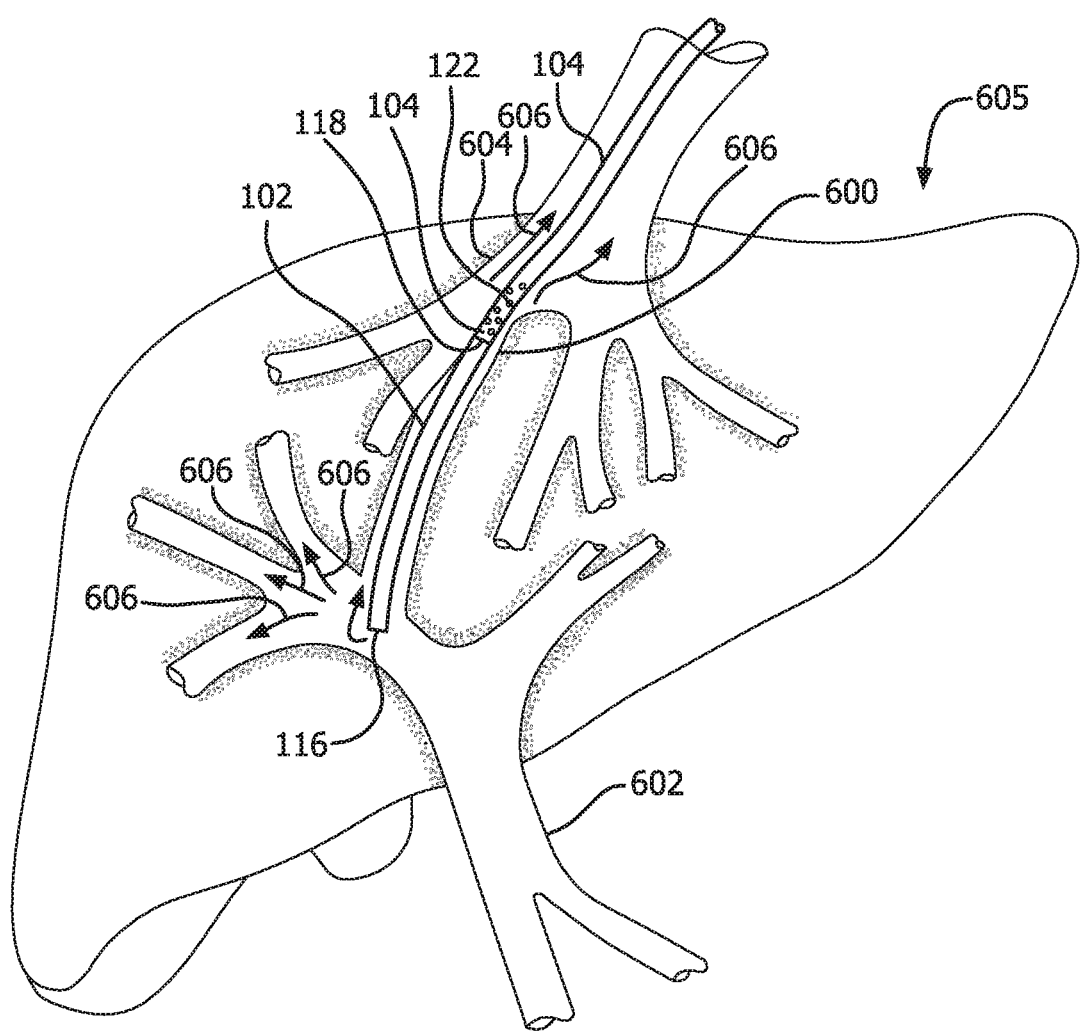
FIGS. 6 and 7 show schematic representations of anatomy that is applicable to use of the catheter assembly in accordance with the present disclosure.

FIG. 6 is a generalized schematic of venous anatomy in proximity of the liver. FIG. 6 generally illustrates a parenchymal tract 600 of the liver 605 between a portal vein 602 and hepatic vein 604. For ease of illustration, not all anatomical features are to scale or represented (e.g., the vena cava), although such anatomical features are well understood as are methods of forming parenchymal tracts (e.g., in association with a Transjugular Intrahepatic Portosystemic Shunt (TIPS) procedure. In some medical procedures, for example in a Transjugular Intrahepatic Portosystemic Shunt (TIPS) procedure, after forming of a liver parenchymal tract 600 (FIG. 6), catheter assembly 100 may be inserted into the vasculature and the tract 600 and utilized to visualize the tract 600 and length of the tract to determine how long of an endoprosthesis may be required to support the tract 600. The catheter assembly 100 is placed in the tract 600 of liver 605 between portal vein 602 and hepatic vein 604. The sheath apertures 122 can be located in the hepatic vein 604 and the catheter assembly distal end 116 can be located in the portal vein 602, allowing fluid to be injected through ports (112, 110 as shown in FIG. 1) and exit sheath apertures 122 and catheter assembly distal end 116 via catheter lumen 119 (may be used as a fluid channel), also as shown in FIG. 1. The fluid can follow blood flow as indicated by arrows 606. The fluid can be injected simultaneously at two different locations along the length of the catheter assembly 100 to visualize the hepatic vein 604 and portal vein 602 at the same time. Alternatively, the fluid can be injected at different times.

In various examples, catheter assembly 100 may incorporate other components. For example, catheter assembly 100 may incorporate an endoprosthesis. The endoprosthesis may be located along the elongated tubular element, (e.g., catheter shaft 102 or perhaps a balloon catheter shaft), between sheath distal end 118 and the elongated tubular element distal end (e.g., catheter assembly distal end 116). This may be advantageous in various ways. For example, it may allow a user to not have to exchange catheter assembly 100 before implanting an endoprosthesis during a medical procedure.

In other medical procedures, for example a procedure where a catheter resides in a vasculature (arterial or venous) for a time sufficient to allow a catheter to adhere to a vessel, catheter assemblies described in the present disclosure may also prove to be useful. For instance, in a TAMBE (Thoracoabdominal Modular Branched Endoprosthesis) procedure, a catheter assembly 100 (as shown in FIG. 7) could undesirably adhere to a vessel 700 (e.g., an iliac artery) at an adhesion, or attachment location 702 during the procedure.

A catheter assembly 100 according to this disclosure would allow a physician or user to inject a fluid into the sheath 104 and exit sheath apertures 122 and catheter assembly distal end 116 to help prevent adhesion to a vessel wall (e.g., by applying preventative hydration at one or more potential adhesion location(s) or by applying preventative hydration at one or more locations upstream of the potential adhesion location(s)). The hydration may hydrate the vessel tissue and/or may hydrate the catheter assembly (e.g., where one or more components of the catheter assembly includes a hydrophilic coating, such as a hydrophilic catheter shaft).

Additionally or alternatively, the catheter assembly 100 may be used to help in releasing the catheter assembly 100 from the vessel (e.g., iliac artery) at adhesion location 702 that the sheath 104 and/or catheter 102 is attached to. The rehydration may hydrate the vessel tissue and/or may rehydrate the catheter assembly (e.g., where one or more components of the catheter assembly includes a hydrophilic coating, such as a hydrophilic catheter shaft). The injected fluid may be dispensed in immediate proximity of the adhesion location for rehydration, or can follow blood flow as indicated by arrows 606.

Figure 7:
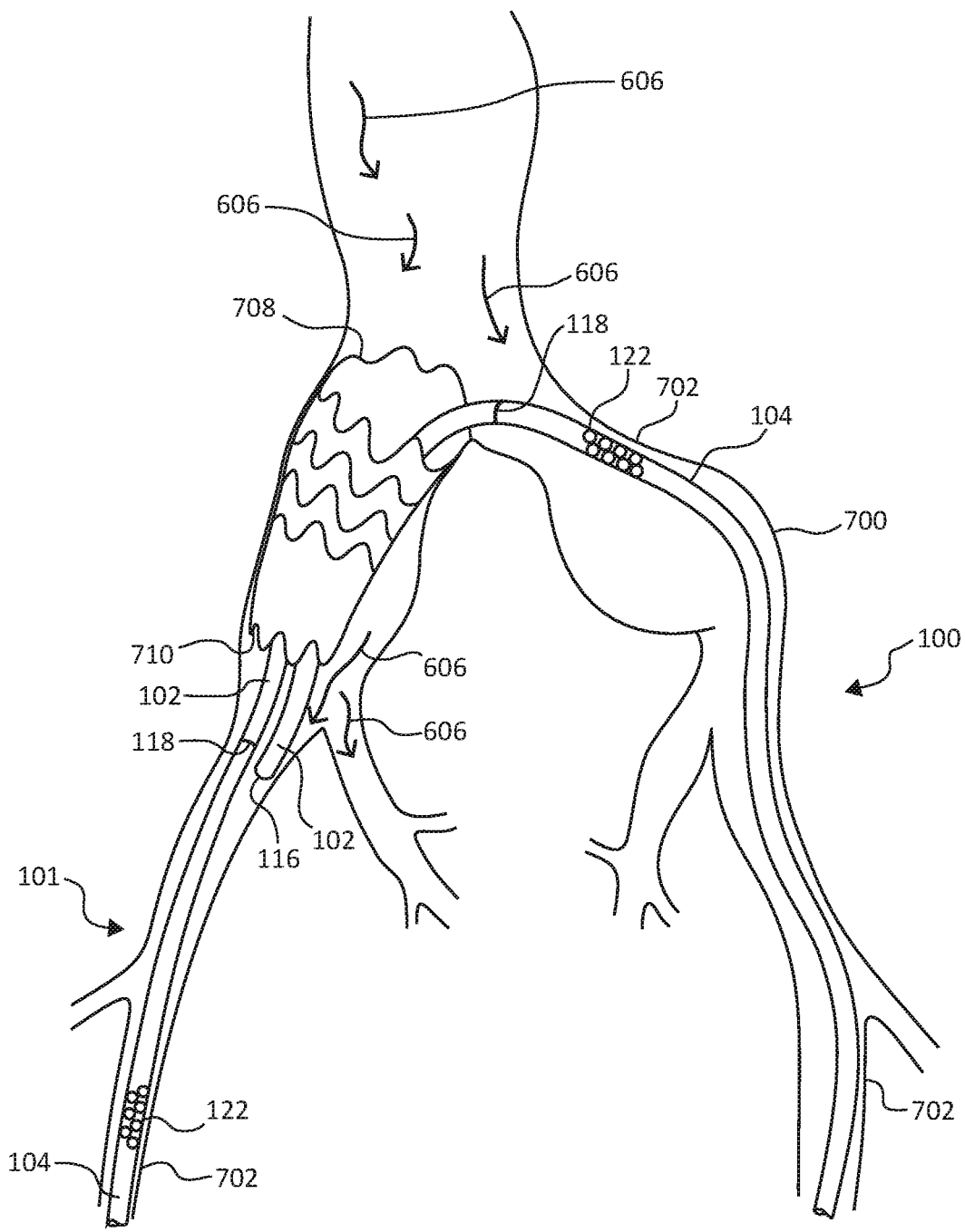

A second catheter assembly 101 in a procedure may become attached at an attachment location 702 as shown in FIG. 7. The injected fluid may help release the catheter assembly 101 from the adhesion location(s) 702. Also, as shown in FIG. 7, catheter assembly 100 could be used in the same TAMBE procedure for imaging purposes. The sheath apertures 122 of sheath 104 may be located near one side of an implant end (e.g., endoprosthesis end 708) and catheter assembly distal end 116 may be located near an implant opposing end (e.g., endoprosthesis end 710). As previously referenced, any of a variety of fluids are contemplated for delivery with catheter assembly 100, including contrast solution, saline, medicaments, blood, serum, or other fluids.

In various examples, the sheath 104 can be utilized to deliver a fluid between sheath inner surface 200 and the catheter outer surface 103. In one example, the sheath can be infused with a contrast solution via one of the fluid delivery ports (112,110), although any of a variety of fluids including saline, medicaments, blood, serum, or other fluids are also contemplated. The fluid is pushed through one of the ports (112,110) to generate internal fluid pressure, along hub fluid space length 127, and along sheath 104 creating a sheath fluid channel 400,401 (e.g., a partial fluid channel or a full fluid channel) as the sheath 104 enlarges (e.g., in diameter as shown in FIGS. 2C, 2D, 4C) between a relaxed or resting state (e.g., diameter) and a full or pressurized state (e.g., diameter). The fluid may flow along the catheter assembly 100, between one of the fluid delivery ports (112,110) and sheath apertures 122, creating a sheath fluid channel 400, 401 between the catheter outer surface 103 and the sheath inner surface 200, until the fluid can exit sheath apertures 122 near the sheath distal end 118. The fluid may also, or alternatively, flow along the catheter assembly 100 and exit catheter assembly distal end 116 via catheter lumen 119. In some examples, the sheath transitions to the pressurized configuration upon application of an internal fluid pressure and returns towards the relaxed configuration and away from the pressurized configuration when the internal fluid pressure is released. When the fluid pressure has been released, (e.g., when the fluid has exited sheath aperture 122) the sheath 104 can retract towards a more relaxed state. The sheath apertures 122 may be between a sheath outer surface 105 and a sheath inner surface 200 and therefore be in a sheath wall. Alternatively, the sheath 104 may have openings formed at the sheath distal end 118, similarly to a partial fluid channel 401 as shown in FIG. 2C.

A catheter assembly according to present disclosure can be manufactured in various ways. One way is as follows. A 4.25 mm OD stainless steel mandrel was obtained and a distensible ePTFE film (e.g., an ePTFE film with an elastomer as taught by US Patent Application Number 2013/0184807 to Kovach et. al.) was obtained. The ePTFE film should have strength in a longitudinal direction, i.e., along length of the mandrel, and be distensible in a circumferential direction relative to the mandrel, in order to enable a fluid space to form when pressurized by an external source. Approximately 4 layers of the ePTFE film were wrapped around the circumference of the mandrel in the fashion of a cigarette wrap with an overlapping edge of the film oriented to be parallel to the longitudinal axis of the mandrel.

After the ePTFE film was wrapped onto the mandrel, loose edges were tacked down with a local heat source (Weller Soldering machine, Apex Tool Group, Apex, N.C. 27539, USA). The ePTFE film was heat treated on the mandrel with a heat source (e.g., a convection oven, Grieves Model NT-1000, The Grieve Corporation, Round Lake, Ill. 60073-2898 USA) for 10 minutes at 300 C. The mandrel with the ePTFE film was removed from the heat source and allowed to air cool. The ePTFE film (now an ePTFE tubular sheath) was removed from the mandrel by sliding the ePTFE tubular sheath off the mandrel. Sheath apertures were formed with a sewing needle that was heated for approximately 1 minute at 250 C. (other methods or tools may be used to create apertures) by penetrating the ePTFE sheath with the heated sewing needle.

A 4 mm outside diameter polymer tube with a 3.33 mm (i.e., 10 French) inner lumen, to be used as the catheter, and a dual port hub (as shown in FIG. 5A), were obtained. The hub was adhered to the polymer tube with an UV cure adhesive (other known methods of adhering a hub to a catheter may be used). The polymer tube had an effective length of 318 mm after the hub was overmolded onto the polymer tube. The ePTFE sheath (sheath) was pulled along the catheter (i.e., polymer tube) and attached to the hub with an adhesive (e.g., cyanoacrylate). The sheath was trimmed approximately 5 mm distal of the apertures in the sheath so the ePTFE sheath had a desired length (293 mm) as measured from end of the sheath to distal end of the hub. The sheath was attached to the catheter with an adhesive (e.g., cyanoacrylate) at the trimmed location. In this way, a catheter assembly having a low profile fixed length sheath capable of being enlarged (e.g., diametrically) to create a fluid space along the sheath; and a catheter with infusion ports where at least one of the infusion ports cooperates with the sheath was made.

In addition to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A catheter assembly having a length comprising:
   an elongate member having a first fluid channel and a length;
   a sheath along the elongate member and selectively attached to the elongate member, the sheath having a first relaxed configuration and a second pressurized configuration and cooperating with the elongate member to form a second fluid channel, wherein the sheath is attached circumferentially to the elongate element at a location distal to at least one macroscopic sheath aperture, wherein the sheath is attached circumferentially to another portion of the catheter assembly at an opposing end of the sheath;
   a first delivery port in communication with the first fluid channel adapted to deliver a fluid through the first fluid channel to a first location along the length of the elongate member; and
   a second delivery port in communication with the second fluid channel adapted to deliver a fluid through the second fluid channel to a second location along the length of the elongate member,
   wherein the sheath is loosely fitted along the elongate member in the first relaxed configuration such that a plurality of sheath pockets are created along the elongate member between the sheath and the elongate member, the plurality of sheath pockets being localized and not running continuously along the sheath.

2. The catheter assembly of claim 1, wherein the sheath is attached to a hub including the first delivery port and the second delivery port.

3. The catheter assembly of claim 1, wherein the elongate member is attached to a hub.

4. The catheter assembly of claim 1, wherein the sheath further comprises a distal end and the sheath is attached to the elongate member near the distal end of the sheath.

5. The catheter assembly of claim 1, wherein the sheath is attached entirely around a portion along the length of the elongate member.

6. The catheter assembly of claim 1, wherein the first relaxed configuration has a circumference around the sheath and the second pressurized configuration has a circumference around the sheath, and the second pressurized configuration circumference around the sheath is greater than the first relaxed configuration circumference around the sheath.

7. The catheter assembly of claim 1, wherein the sheath transitions to the pressurized configuration upon application of an internal fluid pressure and returns towards the relaxed configuration and away from the pressurized configuration when the internal fluid pressure is released.

8. The catheter assembly of claim 1, further comprising an endoprosthesis.

9. The catheter assembly of claim 1, wherein the elongate member is a shaft of a catheter.

10. The catheter assembly of claim 1, wherein the catheter assembly is configured for hydrating biological tissue of a body conduit.

11. A catheter assembly comprising:
    an elongated element with an outer surface, a first end and a second end, a length extending between the first end and the second end, and a lumen extending along the elongated element;
    a sheath surrounding at least a portion of the length of the elongated element;
    wherein the sheath comprises a wall thickness, an outer surface area, and a first relaxed configuration and a second pressurized configuration upon application of an internal fluid pressure within the sheath;
    wherein the sheath is attached circumferentially to the elongated element at a location distal to at least one macroscopic sheath aperture, wherein the sheath is attached circumferentially to another portion of the catheter assembly at an opposing end of the sheath, wherein the sheath cooperates with the elongated element to form a channel when the sheath is in the second pressurized configuration, and wherein the sheath is loosely fitted along the elongated element in the first relaxed configuration such that a plurality of sheath pockets are created along the elongated element between the sheath and the elongated element, the plurality of sheath pockets being localized and not running continuously along the sheath; and
    wherein said at least one macroscopic sheath aperture has a macroscopic sheath aperture area that occupies 20% or less of surface area of the sheath.

12. The catheter assembly of claim 11, wherein the sheath returns towards the relaxed configuration and away from the pressurized configuration when the internal fluid pressure is released.

13. The catheter assembly of claim 11, wherein there are multiple macroscopic sheath apertures clustered along a location near a distal end of the sheath.

14. A multi-channel catheter assembly having a length comprising:
    an elongate member having a first fluid channel;
    a sheath along the elongate member, the sheath having a first relaxed configuration and a second pressurized configuration and cooperating with the elongate member to form a second fluid channel, wherein the sheath is attached circumferentially to the elongated element at a location distal to at least one macroscopic sheath aperture, wherein the sheath is attached circumferentially to another portion of the catheter assembly at an opposing end of the sheath;

a first delivery port in communication with the first fluid channel; and a second delivery port in communication with the second fluid channel, wherein the sheath is loosely fitted along the elongate member in the first relaxed configuration such that a plurality of sheath pockets are created along the elongate member between the sheath and the elongate member, the plurality of sheath pockets being localized and not running continuously along the sheath.

15. The catheter assembly of claim 14, wherein the sheath is attached to a hub including the first delivery port and the second delivery port.

* * * * *